United States Patent
Saffroy et al.

(10) Patent No.: US 10,385,401 B2
(45) Date of Patent: Aug. 20, 2019

(54) METHOD FOR DETECTING CHROMOSOMAL REARRANGEMENTS

(71) Applicant: Assistance Publique Hopitaux de Paris, Paris (FR)

(72) Inventors: Raphael Saffroy, Paris (FR); Antoinette Lemoine, Marne la Coquette (FR)

(73) Assignee: Assistance Publique Hopitaux de Paris, Paris (FR)

( * ) Notice: Subject to any disclaimer, the term of this patent is extended or adjusted under 35 U.S.C. 154(b) by 254 days.

(21) Appl. No.: 15/038,122

(22) PCT Filed: Nov. 21, 2014

(86) PCT No.: PCT/EP2014/075318
§ 371 (c)(1),
(2) Date: May 20, 2016

(87) PCT Pub. No.: WO2015/075196
PCT Pub. Date: May 28, 2015

(65) Prior Publication Data
US 2016/0319365 A1    Nov. 3, 2016

(30) Foreign Application Priority Data
Nov. 21, 2013  (EP) .................................... 13306589

(51) Int. Cl.
*C12Q 1/68* (2018.01)
*C07H 21/00* (2006.01)
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2600/118* (2013.01); *C12Q 2600/156* (2013.01); *C12Q 2600/16* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 7,005,265 B1 * | 2/2006 | Fan ...................... | C12Q 1/6844 435/287.2 |
| 7,198,893 B1 | 4/2007 | Koster et al. | |
| 7,501,251 B2 | 3/2009 | Koster et al. | |
| 9,611,283 B1 * | 4/2017 | Zhang ................. | A61K 31/675 |
| 2009/0239764 A1 * | 9/2009 | Sparks ................. | C12Q 1/6827 506/9 |

FOREIGN PATENT DOCUMENTS

| | | |
|---|---|---|
| WO | 1997/037041 A2 | 10/1997 |
| WO | 2007/084631 A2 | 7/2007 |
| WO | 2011/140187 A2 | 11/2011 |

OTHER PUBLICATIONS

Iafrate et al., Detection of large-scale variationin the human genome. Nature Genetics 36(9) : 949 (Year: 2004).*
Kaminski et al.,131I-Tositumomab Therapy as Initial Treatment for Follicular Lymphoma. New England J. of Medicine 352 (5) :441 (2005). (Year: 2000)*
Kokorisa et al., Molecular Diagnosis 5(4) : 329 (Year: 2000).*
Kong et al.,dbCRID: a database of chromosomal rearrangements in human diseases. Nucleic Acids Research 39: D895 (Year: 2011).*
Korbel et al., Paired-End Mapping Reveals Extensive Structural Variation in the Human Genome. Science 318 :420 (Year: 2007).*
Palanisamy et al., Rearrangements of the RAF kinase pathway in prostate cancer, gastric cancer and melanoma. Nature Medicine 16(7) : 793 (Year: 2010).*
Shaw et al.,Clinical Features and Outcome of Patients With Non-Small-Cell Lung Cancer Who Harbor EML4-ALK. J. of Clinical Oncology 27(26) : 4247 (Year: 2009).*
Steidl et al., MHC class II transactivator CIITA is a recurrent gene fusion partner in lymphoid cancers. Nature 471: 377 (Year: 2011).*
Yoshida et al., Immunohistochemical detection of ROS1 isuseful for identifying ROS1 rearrangements in lung cancers. Modern Pathology 27 :711 (published online Nov. 1, 2013). (Year: 2013).*
Zhang et aL., Complex human chromosomal and genomic rearrangements. Trends in Genetics 25(7) :298 (Year: 2009)*
Bergethon et al.; Journal of Clinical Oncology; 2012; 30:8 863-870.
Chamberlain et al., Nucleic Acids Research; 16 (23): 11141-11156, 1988.
Crain et al. (Mass Spectrometry Reviews, 9, 505-554; 1990).
Huijsmans1 et al., BMC Research Notes, 3:239, 2010.
Jahr et al., Cancer Res. 61: 1659-1665, 2001.
Koivunen et al.; Clin Cancer Res.; 2008; 14(13): 4275-4283.
Mouliere et al., PLoS One.;6(9):e23418, 2011.
Neddleman and Wunsch (1970) J. Mol. Biol. 48:443.

(Continued)

*Primary Examiner* — Ethan C Whisenant
(74) *Attorney, Agent, or Firm* — Banner & Witcoff, Ltd.

(57) ABSTRACT

An object of the invention is an in vitro method for detecting chromosomal rearrangements between at least two specific chromosomal regions in a biological sample of a human subject, which comprises the steps of: a) isolating deoxyribonucleic acid (DNA) molecules comprising said specific chromosomal regions from said biological sample, wherein said DNA molecules have an average length of X base pairs; b)amplifying the DNA molecules of step a) by a multiplex polymerase chain reaction assay, said assay comprising at least two sets of primers, wherein each set of primers is capable of hybridizing with a specific reference chromosomal region, and each set of primer comprises a plurality of primers, said primers being capable of hybridizing to a nucleic acid strand of one of the said specific chromosomal regions at sites regularly spaced of less than X/2 base pairs; and hybridizing the product of the amplification of step b) with at least one set of nucleic probes.

19 Claims, 2 Drawing Sheets

Figure 1:
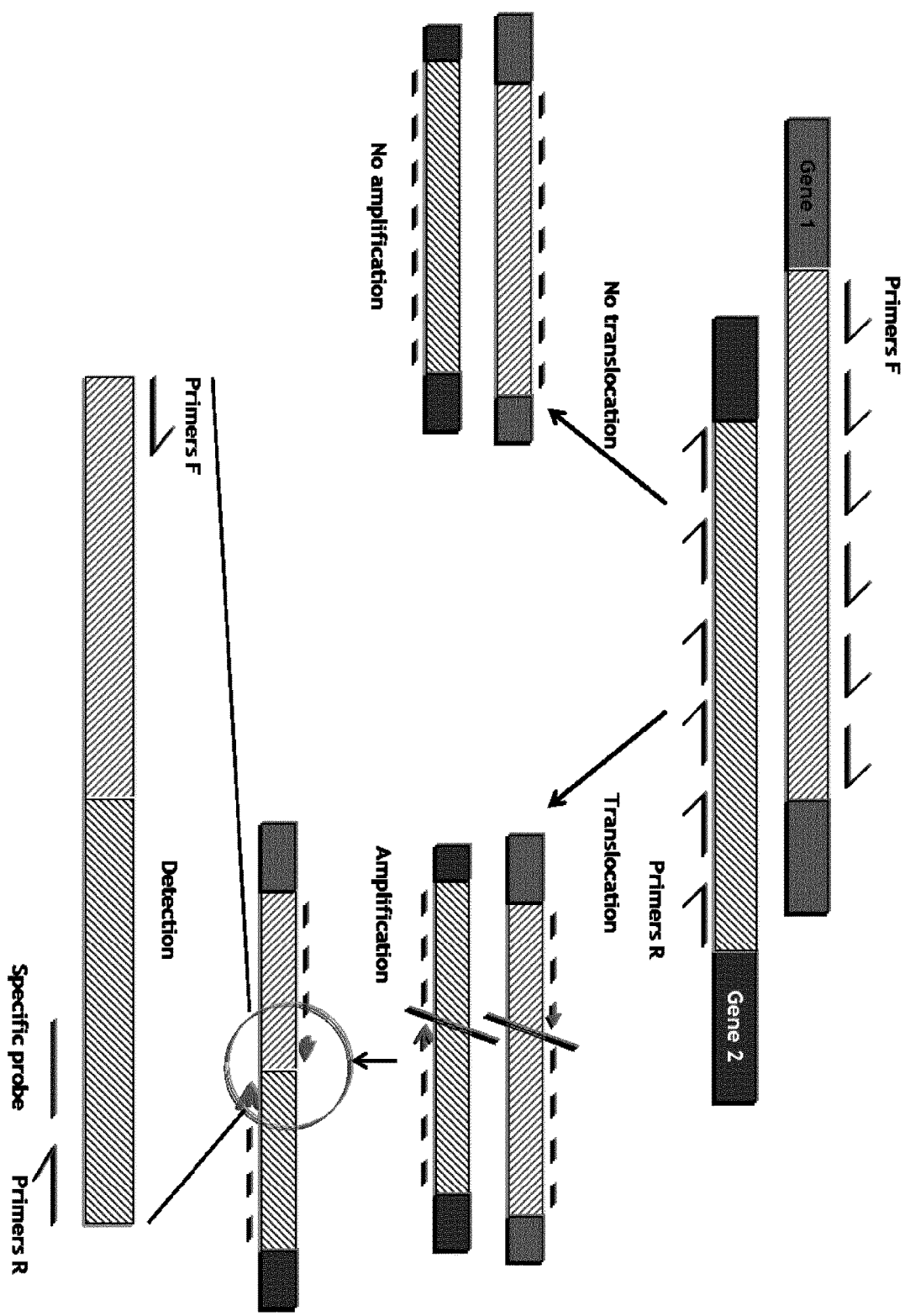

Specification includes a Sequence Listing.

(56) References Cited

OTHER PUBLICATIONS

Pearson and Lipman (1988) Proc. Natl. Acad. Sci. USA 85:2444.
Sato, et al. "Comparison of the DNA Extraction Methods for Polymerase Chain Reaction Amplification from Formalin-Fixed and Paraffin-Embedded Tissues," Diagnostic Molecular Pathology; 10: 4; 265-271; 2001.
Schwarzenbach et al., Nat Rev Cancer. 11(6): 426-437, 2011.
Shaw et al., N Engl J Med. Sep. 27, 2014. [Epub ahead of print].
Singh et al, Science. Sep. 7, 2012;337(6099):1231-5. doi: 10.1126.
Smith and Waterman (1981) [Ad. App. Math. 2:482.
Tatusova et al., FEMS Microbiol., 1999, Lett. 174:247-250.

International Search Report Issued in Corresponding International Application No. PCT/EP2014/075318, dated Feb. 23, 2015.
Cai et al., ROS1 Fusions in Chinese Patients With Non-Small-Cell Lung Cancer, Annals of Oncology, vol. 24, No. 7, Mar. 20, 2013, pp. 1822-1827.
Ming-Tseh Lin et al., D-PCR, A Simple Method to Detect Translocations and Insertion/Deletion Mutations, The Journal of Molecular Diagnostics, vol. 13, No. 1, Jan. 2011, pp. 85-92.
Soda et al., A Prospective PCR-Based Screening for the EML4-ALK Oncogene in Non-Small Cell Lung Cancer, Clinical Cancer Research, vol. 18, No. 20, Oct. 15, 2012, pp. 5682-5689.
Spence et al., Demonstration of Array-Based Analysis for Highly Multiplexed PCR Assays, Journal of Molecular Diagnostics, vol. 13, No. 3, May 2011, pp. 252-262.

\* cited by examiner

METHOD FOR DETECTING CHROMOSOMAL REARRANGEMENTS

RELATED APPLICATION DATA

This application is a National Stage Application under 35 U.S.C. 371 of co-pending PCT application number PCT/EP2014/075318 designating the United States and filed Nov. 21, 2014; which claims the benefit of EP application number 13306589.6 and filed Nov. 21, 2013, each of which are hereby incorporated herein by reference in their entireties.

Numerous chromosomal rearrangements have been associated with the development of particular pathologies. Interestingly, some rearrangements have also been associated with a greater sensitivity to specific treatments.

For example, chromosomal rearrangements that fuse various 5' partners with the 3' kinase domain of the anaplastic lymphoma kinase (ALK) gene, have been described in several malignancies, including non-small cell lung cancer (NSCLC). In humans, the echinoderm microtubule-associated protein-like 4 (EML4) gene, the kinesin family member 5B (KIF5B) gene and the TRK-fused (TFG) gene have been found to be fusion partners for the ALK gene. In lung cancer, the most common 5' fusion partner for the ALK gene is the EML4 gene.

More particularly, it has been shown that a subset of cancer like non-small cell lung cancer (NSCLC) patients harbors rearrangements between the ALK gene and the EML4 gene that lead to a fusion gene called the EML4-ALK fusion oncogene. It was further demonstrated that such rearrangements are associated with an increased efficacy of ALK kinase inhibitors in the treatment of non-small cell lung cancers (Koivunen et al.; Clin Cancer Res.; 2008; 14(13): 4275-4283).

In addition, chromosomal rearrangements involving the proto-oncogene tyrosine-protein kinase gene ROS1 have also recently been described in a subset of non-small-cell lung cancers, and also seem to correlate with a greater sensitivity to the anti-cancer drug crizotinib (Bergethon et al.; Journal of Clinical Oncology; 2012; 30:8 863-870). More specifically, crizotinib seems to show high activity in patients with advanced ROS1-rearranged NSCLC; hence, ROS1 rearrangements, e.g. with CD74, EZR, or SLC34A2, seems to define a second molecular subgroup of NSCLC for which crizotinib is highly active in cancer samples seem to be associated with a good response to the anti-cancer drug crizotinib (see e.g. Shaw et al., N Engl J Med. 2014 Sep. 27. [Epub ahead of print]).

Other chromosomal rearrangements, involving other genes than ALK or ROS have also been identified as potentially targeted by drugs. These are for example FGFR3-TACC3 (Singh D1, Chan J M, Zoppoli P, Niola F, Sullivan R, Castano A, Liu E M, Reichel J, Porrati P, Pellegatta S, Qiu K, Gao Z, Ceccarelli M, Riccardi R, Brat D J, Guha A, Aldape K, Golfinos J G, Zagzag D, Mikkelsen T, Finocchiaro G, Lasorella A, Rabadan R, lavarone A., Science. 2012 Sep. 7; 337(6099):1231-5. doi: 10.1126). The provisions of sensitive methods for the detection of chromosomal rearrangements, for example in a tumor sample from a patient, is thus critical for both diagnosis and prognosis purposes.

Chromosomal rearrangement are often caused by a breakage in the DNA (deoxyribonucleic acid) double helix at two different locations, followed by a rejoining of the broken ends to produce a new chromosomal arrangement of genes, different from the gene order of the chromosomes before they were broken. The breakage in the DNA may occur at various locations among individuals.

For instance, chromosomal rearrangements leading to the formation of the EML4-ALK fusion oncogene do not always occur at the same rupture point. At least 11 EML4-ALK protein variants have been reported to date and several of them have already been correlated with an increased efficacy of ALK kinase inhibitors, more particularly of the anti-cancer drug crizotinib. Those EML4-ALK variants include at least EML4-ALK E6;A19, EML4-ALK E6;A20, and EML4-ALK E13;A20.

The resulting change in the sequence of the DNA thus cannot be anticipated. This uncertainty regarding the location of the rupture point imposes limitations on the techniques that can be used to detect the chromosome rearrangement. It makes it difficult for example to design appropriate primer sets for amplifying the rearranged DNA, and as a consequence to rely on techniques based on polymerase chain reaction (also called PCR-based techniques).

Moreover, and particularly in the case of malignancies, the techniques available to the skilled person for the detection of chromosomal rearrangements are narrowed by technical issues associated with the quantity and quality of the biological sample to be analyzed.

For instance, when the tumor is a solid lesion, a biopsy sample may be necessary for the detection of the rearrangements. Biopsy samples are very often treated to ensure preservation following collection, which may involve fixation of the tissue sample, thereby causing DNA fragmentation and cross-linking.

For example, formalin-fixed paraffin-embedded (FFPE) preparation is the worldwide most simple and therefore most frequently applied method of biobanking by the pathologists, as well as the standard reference material used for the primary histological diagnosis of cancer by histopathologists. FFPE samples thus represent the most commonly used source of biological material for the detection of chromosomal rearrangements in solid tumors. However, the DNA present in FFPE samples is not intact: the average size of DNA fragments in paraffin-embedded tissue samples ranges from about 200 to 600 base pairs.

Lately, cell-free DNA found in blood and blood-derived samples has also been used to detect mutations or rearrangements in patients, since it is known that circulating ("cell-free") tumor DNA may also be found in samples such as blood, plasma or serum. Yet, cell-free DNA is usually scarce and fragmented (Mouliere et al., *PLoS One.*; 6(9):e23418, 2011). Indeed, it is known that the average size of cell-free DNA fragments ranges from about 70 to 200 base pairs, although fragments as large as 10,000 bp could also be identified (Jahr et al., *Cancer Res.* 61: 1659-1665, 2001; Schwarzenbach et al., *Nat Rev Cancer.* 11(6): 426-437, 2011).

Thus, in most cases, the person skilled in the art is confronted with the scarcity of biological material, and thus is limited to detection techniques that can provide a specific and sensitive detection with very little of the biological sample. Furthermore, in most type of relevant samples, the available DNA is fragmented.

Moreover, because of the random position of the breakage, PCR-based techniques detecting chromosome rearrangements must be long range PCR-based techniques requiring DNA sufficiently preserved. These methods are not applicable to FFPE DNA. DNA fragmentation reduces the sensitivity of PCR-based techniques, as the locus of interest may not be amplified or may not hybridize with the primers correctly.

For the above reasons, the most commonly used methods for detecting chromosome rearrangements are either FISH techniques, or RT-PCR on mRNA extracted from the samples.

FISH (fluorescence in situ hybridization) is a cytogenetic technique, which is often used for finding specific features in DNA. FISH uses fluorescent probes that bind to only those parts of the chromosome with which they show a high degree of sequence complementarity with. FISH can be used to detect and localize the presence or absence of specific DNA sequences on chromosomes, and thus chromosome rearrangements. Its implementation however requires highly trained technicians and physicians, comprises many steps and remains difficult to interpret.

As for RT-PCR on mRNA, it cannot be systematically used as a routine technique. Indeed, there is very little amount of mRNA in samples such as paraffin-embedded tissue sample, mRNAs could be damaged by formol fixation and paraffin embedding. The difficulty of this technique will be correlated to the number of variants. This technique can only be used as a confirmation of a diagnosis when the quantity of sample is limited.

There is thus still a need for improved methods to detect easily and rapidly chromosome rearrangements that would be suited for use when the DNA in the sample is scarce and/or fragmented. Such methods would be extremely beneficial, as they would then allow diagnosis or prognosis to be made with samples such as paraffin-embedded tissue samples or blood derived samples and in particular samples comprising cell-free DNA derived from blood.

Finally, due to the increased high number of samples that require such diagnosis worldwide, there is also the need to develop method of chromosomal breakpoints rearrangements detection adapted to a high throughput diagnosis.

FIGURE LEGENDS

FIG. 1 illustrates the method of the invention. See the text for details

Figure 2:
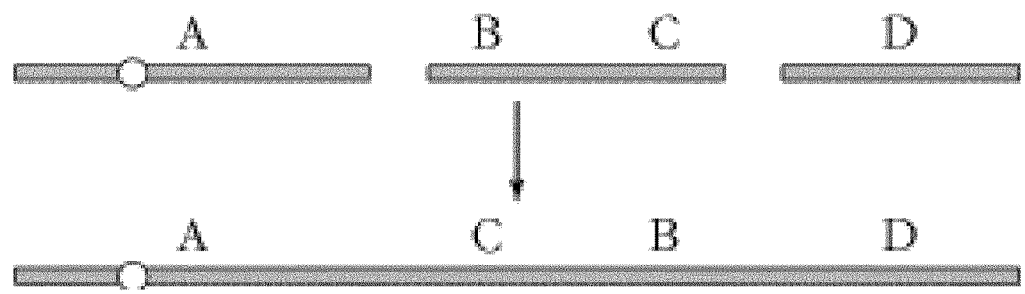

FIG. 2 illustrates molecular events that may lead to an inversion. A segment of a DNA molecule is broken twice (once at each end of said segment), flipped 180 degrees, and rejoined. The lower band represents the DNA molecule resulting from such molecular events.

Figure 3:
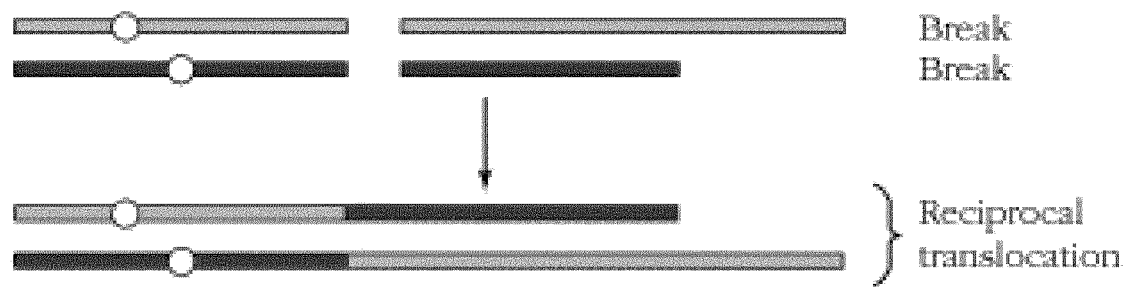

FIG. 3 illustrates molecular events that may lead to a reciprocal translocation. A first chromosome is broken, a segment of a second chromosome is broken, and the segment of the first chromosome is joined to the second chromosome, while the segment of the second chromosome joins the first chromosome. The two lower bands represent the DNA molecules resulting from such molecular events.

DETAILED DESCRIPTION

The inventors have designed a method for detecting chromosome rearrangements that is highly sensitive and very simple to implement. The method of the invention can be performed even when the amount of biological sample is scarce. In addition, the method of the invention can be used for multiplexing, independently of the amount of sample available. Further, the method of the invention can overcome technical issues associated with fragmented DNA. The method of the invention can thus be used even when the quality of the DNA contained in the sample is not guaranteed. Importantly, the method of the invention also enables the direct determination of the breakage point by sequencing.

The method of the invention relies on PCR-based techniques for detecting chromosome rearrangements that occur between at least two specific chromosomal regions. The main advantages of PCR-based techniques are their speed and simplicity of use, the low amounts of DNA required can be performed on the same DNA extracted for mutation screening, and the possibility to use DNA of low quality. Consequently, the method of the invention can be used even when the amount of biological sample is scarce, or when the quality of the DNA it contains is low. For example, the method of the invention allows the use of small biopsies (such as fine needle aspiration biopsies), or the use of formaldehyde-fixed paraffin-embedded samples, which generally results in DNA of low quality.

The method of the invention is illustrated in FIG. 1. Said method uses at least two primer sets, each one comprising primers that hybridize with only one of the two specific chromosomal regions of interest. The primers within a set hybridize and anneal with only one strand of said one of the two specific chromosomal regions of interest.

When the sample does not actually contains a rearrangement between the two specific chromosomal regions of interest, the distance between the chromosomal regions of interest, where the two primer sets hybridize, will be too important to enable amplification of the DNA.

Indeed, in the absence of chromosomal rearrangements between the two specific chromosomal regions of interest, those two regions are not adjacent to each other. Indeed, they are either apart on the same chromosome, or located on two different chromosomes. Yet, because the biological sample to be used is expected to contain fragmented DNA, it is unlikely that it actually contains a fragment that comprises the two chromosomal regions of interest. Consequently, in the absence of chromosomal rearrangement between the two specific chromosomal regions of interest in the biological sample, the PCR will be impaired and will not raise any amplification product.

On the other hand, when the sample actually contains a rearrangement between the two specific chromosomal regions of interest, the distance between the regions where the two primer sets hybridize will be short enough to enable DNA amplification.

Indeed, when the sample comprises a chromosomal rearrangement between the two specific chromosomal regions of interest, said two specific chromosomal regions of interest are then adjacent to each other. In that case, it is likely that primers from both primer sets will be able to anneal to at least one fragment of DNA, and thus enable DNA amplification.

Hence, particularly when using fragmented DNA, the PCR will only raise an amplification product when the biological sample comprises a chromosomal rearrangement between the two specific chromosomal regions of interest.

The method of the invention is thus both highly sensitive and highly specific. In general, the sensitivity of a method measures the ability of the latter to give a positive result when a hypothesis is true, while the specificity measures the ability of a test to give a negative result when the assumption is false. Thus, the sensitivity of a method of detection is estimated by the proportion of samples identified as positive (that is to say as comprising a specific feature) by the method, in samples actually comprising such a feature. The specificity of a method of detection is estimated by the proportion of samples identified as negative (that is to say as not comprising a specific feature) by the method, in samples actually not comprising such a feature.

Detection of rearrangements between two chromosomal regions by PCR-based techniques usually requires precise knowledge of the rearranged segments in order to design appropriate primers at opposite sides of the rupture point.

The invention however does not require such information, as the two sets of primers allow the detection of any rearrangements between two chromosomal regions without previous knowledge of the precise location of the rupture point(s).

A first object of the invention is an in vitro method for detecting chromosomal rearrangements between at least two specific chromosomal regions in a biological sample of a human subject, which comprises the steps of:
 a) isolating deoxyribonucleic acid (DNA) molecules comprising said specific chromosomal regions from said biological sample, wherein said DNA molecules have an average length of X base pairs;
 b) amplifying the DNA molecules of step a) by a multiplex polymerase chain reaction assay,
said assay comprising at least two sets of primers, wherein each set of primers is capable of hybridizing with a specific reference chromosomal region, and
each set of primer comprises a plurality of primers,
said primers being capable of hybridizing to a nucleic acid strand of one of the said specific chromosomal regions at sites regularly spaced of less than X/2 base pairs; and
hybridizing the product of the amplification of step b) with at least one set of nucleic probes.

By "chromosomal rearrangement" it is herein referred to an aberration of the genome resulting from a change in the structure of at least one chromosome, wherein the sequence of the rearranged chromosome is different from the sequence of reference for said chromosome. In the context of the invention, the term "chromosomal rearrangement" encompasses deletions, duplication, inversions, and translocations. By "the sequence of reference for said chromosome" it is herein referred to the sequence for that chromosome present in the majority of human subjects. In the context of the invention, the term "the sequence of reference for said chromosome" encompass sequences of human chromosomes indexed in the Genome Reference Consortium Human Build 37 patch release 12 (GRCh37.p12). Such sequences of reference are well known from the person skilled in the art, and are for example displayed in databases such as the "GENE" database hosted by NCBI (available at the address: http://www.ncbi.nlm.nih.gov/genome/guide/human).

By "deletion" it is herein referred to an aberration of the genome in which one or more nucleotides are missing in a sequence of a chromosome or of a DNA molecule, compared to the sequence of a chromosome or of a DNA molecule of reference.

By "duplication" it is herein referred to an aberration of the genome in which one or more contiguous nucleotides are found in two copies in a sequence of a chromosome or of a DNA molecule, compared to the sequence of a chromosome or of a DNA molecule of reference wherein the same nucleotide are only found in one copy.

By "inversion" it is herein referred to an aberration of the genome in which a segment of the sequence of a chromosome or of a DNA molecule is reversed end to end, compared to a sequence of reference of said chromosome or of said DNA molecule.

For example, an inversion may result from a molecular event in which a segment of a DNA molecule is broken twice (once at each end of said segment), flipped 180 degrees, and rejoined, such as illustrated in FIG. 2. Consequently, the sequence of the chromosome comprising the inversion is different from the sequence of reference of said chromosome in that a segment of the sequence of the chromosome after inversion is reversed end to end.

By "translocation" it is herein referred to an aberration of the genome in which a segment of a chromosome is exchanged with a segment of a separate non-homologous chromosome. According to the invention, the term "translocation" encompasses reciprocal translocation and Robertsonian translocation. By "reciprocal translocation", it is herein referred to a translocation in which the segments of chromosomes that are exchanged are acentric segments of said chromosomes. By "Robertsonian translocation", it is herein referred to a translocation in which segments of chromosomes that are exchanged are acrocentric segments of said chromosomes. By "acentric segment" it is herein referred to a segment of a chromosome that lacks a centromere. By "acrocentric segment" it is herein referred to a segment of a chromosome that comprises a centromere. By "centromere" it is herein referred to the part of a chromosome that links sister chromatids. The centromere of a chromosome can easily be detected, for example by analyzing a karyotype by microscopy, after coloration by Giemsa. Under microscopy, the centromere of a chromosome in a karyotype appears as a constricted region of the chromosome where the two sister chromatids are most closely in contact. By "chromatid" it is herein referred to one copy of a duplicated chromosome. By "sister chromatids" it is herein referred to two copies of a duplicated chromosome that are joined by the centromeres.

For example, a reciprocal translocation may occur after a molecular event in which a segment of a first chromosome is broken, a segment of second chromosome, which is a separate chromosome non-homologous to the first chromosome segment, is broken, and the segment of the first chromosome is joined the second chromosome, while the segment of the second chromosome is joined to the first chromosome, such as illustrated in FIG. 3.

Preferably, the chromosomal rearrangement according to the invention is an inversion or a translocation. In an embodiment, the chromosomal rearrangement according to the invention is an inversion. In another embodiment, the chromosomal rearrangement according to the invention is a translocation.

By "specific chromosomal region" it is herein referred to a specific part of a chromosome defined either by anatomical details, such as banding, or by its nucleotide sequence, such as the genes it comprises.

Many human cancers are associated with characteristic chromosomal rearrangements, especially hematopoietic cancers such as leukemias and lymphomas, but also solid cancers. Various genes, such as e.g. FGFR3, TACC3, BCL-2, E2A, ALL, ABL, BCR, PBX-1, are involved in such rearrangements. In particular, chromosomal rearrangements involving either the anaplastic lymphoma kinase gene (ALK) or the proto-oncogene tyrosine-protein kinase gene (ROS1) have been described for lung cancer. Therefore, said reference chromosomal regions comprise at least one region comprising at least of the genes involved in a cancer-associated chromosomal rearrangement. Preferentially, said reference chromosomal regions comprise at least one region selected from the anaplastic lymphoma kinase gene (ALK) of sequence SEQ ID No.1 and the proto-oncogene tyrosine-protein kinase gene ROS1 of sequence SEQ ID No.5.

As mentioned above, chromosomal rearrangements (inversions and translocations) that fuse various 5' partners with the 3' kinase domain of ALK have been described in several malignancies, including non-small cell lung cancers. In humans, the ELM4 gene (NCBI references: 27436) encodes the Echinoderm microtubule-associated protein-like 4, the KIF5B gene (NCBI references: 3799) encodes the Kinesin-1 heavy chain protein and the TRK-fused gene, also called the TFG gene (NCBI references: 10342), encodes the protein TFG. All of those genes have been found to be fusion partners for the ALK gene. In lung cancer, the most common 5' fusion partner for ALK is EML4.

The detection of chromosomal rearrangements involving those genes is thus of critical importance, particularly in the prognosis of lung cancer.

In an embodiment, said reference chromosomal regions comprise at least the anaplastic lymphoma kinase gene (ALK) of sequence SEQ ID No.1.

In a preferred embodiment, said reference chromosomal regions comprise at least the anaplastic lymphoma kinase gene (ALK) of SEQ ID No.1 and the kinesin family member 5B gene (KIF5B) of sequence SEQ ID No.2.

In another preferred embodiment, said reference chromosomal regions comprise at least the anaplastic lymphoma kinase gene (ALK) of SEQ ID No.1 and the TFG gene (TFG) of sequence SEQ ID No.3.

In yet another preferred embodiment, said reference chromosomal regions comprise at least the anaplastic lymphoma kinase gene (ALK) of SEQ ID No.1 and the echinoderm microtubule-associated protein-like 4 gene (EML4) of sequence SEQ ID No.4.

On the other hand, chromosomal rearrangements involving the Proto-oncogene tyrosine-protein kinase gene ROS1 have also recently been described in a subset of non-small-cell lung cancers, as well as in other cancers like chlangio-carcinomas or melanomas. The presence of such rearrangements seems to correlate with a greater sensitivity to the anti-cancer drug crizotinib (Bergethon et al.; *Journal of Clinical Oncology*; 2012; 30:8 863-870). As mentioned above, chromosomal rearrangements involving ROS1 and either the CD74, EZR or SLC34A2 gene in cancer samples seem to confer high sensitivity to the anti-cancer drug like crizotinib, but rearrangements involving ROS1and other genes are also known. Methods for determining the presence of such rearrangements in biological sample are therefore of particular interest.

In humans, the CD74 gene (NCBI reference: 972) encodes the HLA class II histocompatibility antigen gamma chain, also known as HLA-DR antigens-associated invariant chain or CD74 protein; the EZR gene (NCBI reference: 7430) encodes the ezrin protein, also known as cytovillin or villin-2; and the SLC34A2 gene (NCBI reference: 10568), encodes the sodium-dependent phosphate transport protein 2B. All of those genes have been found to be fusion partners for the ROS1 gene.

Thus, in another embodiment, said reference chromosomal regions comprise the proto-oncogene tyrosine-protein kinase gene ROS1 of sequence SEQ ID No.5.

In a preferred embodiment, said reference chromosomal regions comprise the proto-oncogene tyrosine-protein kinase gene ROS1 of sequence SEQ ID No.5 and the CD74 gene (CD74) of sequence SEQ ID No.312.

In another preferred embodiment, said reference chromosomal regions comprise the proto-oncogene tyrosine-protein kinase gene ROS1 of sequence SEQ ID No.5 and the EZR gene (EZR) of sequence SEQ ID No.313.

In yet another preferred embodiment, said reference chromosomal regions comprise the proto-oncogene tyrosine-protein kinase gene ROS1 of sequence SEQ ID No.5 and the SLC34A2 gene (SLC34A2) of sequence SEQ ID No.314.

The method of the invention is performed using a biological sample of the subject to be tested. In an embodiment, the method of the invention further comprises a preliminary step of taking a biological sample from the subject. The term "subject" refers to a human and includes male and female subjects. In the sense of the present invention, the terms "patient" or "subject" may be used interchangeably.

According to the invention, the term "biological sample" refers to a sample of biological tissue from a subject, its cells or component parts, which comprise DNA from said subject. "A biological sample" further refers to a homogenate, lysate or extract prepared from a sample of biological tissue from a subject, its cells or component parts, or a fraction or portion thereof, that comprise DNA from said subject. Preferably, the DNA from said subject is genomic DNA. By "genomic DNA" it is herein referred to deoxyribonucleic acids which sequence is identical to that of the genome of the subject. The terms "genomic DNA" encompass DNA that may have undergone purification, or fragmentation. Most often, the biological sample has been removed from a subject. Biological samples can be collected from a subject using any standard method known in the art that results in the preservation of nucleic acids.

The method of the invention can be used to analyze any type of biological sample comprising chromosomal DNA. Yet, it is particularly appropriate for detecting chromosomal rearrangement in biological samples comprising fragmented DNA. For example, the method of the invention is particularly suited for detecting chromosomal rearrangements in samples obtained from solid tumors. Thus, in an embodiment, the biological sample is a tissue sample. In a preferred embodiment, the biological sample is a tumor tissue.

It is further well known that circulating tumor DNA may also be found in liquid samples such as blood, plasma or serum. Although conventional tumor biopsies are preferable, these often cannot be obtained for logistic or medical reasons. When tumor tissue specimens from patients are unavailable, liquid samples offer an alternative that can be rapidly implemented without the pain, risk, and expense entailed by a biopsy of one of the metastatic lesions. As such DNA is usually scarce and fragmented (Mouliere et al., *PLoS One.*; 6(9):e23418, 2011), the method of the invention is of particular interest for detecting chromosomal rearrangement in this type of sample. Moreover FISH or imunohistochemistry are not applicable in this kind of samples. In another embodiment, the biological sample is a blood-derived sample, such as e.g. blood, plasma or serum.

The method of the invention is suited for detecting chromosomal rearrangement in any type of tissue or of tumor.

In an embodiment, said tumor is selected from the group consisting of carcinoma, including that of the bladder, brain, breast, colon, kidney, liver, lung, ovary, pancreas, stomach, cervix, thyroid and skin; including squamous cell carcinoma; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma.

Of particular interest in the invention are lung cancers. Indeed, as explained above, lung cancer patients, and particularly non-small-cell lung cancer patients (also called non-small-cell lung carcinoma patients) may harbor specific chromosomal rearrangement correlated with a greater sensitivity to specific treatments.

According to the invention lung cancer comprises non-small-cell lung cancer, small-cell lung cancer, glandular tumors, carcinoid tumors, and undifferentiated carcinomas.

According to the invention non-small-cell lung cancer comprises adenocarcinoma, squamous-cell lung carcinoma, and large-cell lung carcinoma.

Preferably, the biological sample is a tumor tissue wherein the tumor is lung cancer. Yet preferably, the biological sample is a tumor tissue wherein the tumor is non-small-cell lung cancer.

Tissue samples, particularly tumor tissue, may be obtained for example from biopsies from the subject. Biopsies can be collected using standard techniques such as needle biopsy or surgical excision.

Alternatively, the biological sample may be a blood-derived sample, such as blood, plasma or serum. Such a kind of sample is known to contain cell-free tumor DNA and can be easily collected by methods known in the art.

According to the invention, the biological sample can be assayed for chromosomal rearrangements in a target DNA sequence immediately following collection. Alternatively, or in addition, a biological sample can be stored for later analysis using methods known in the art. For example, a sample can be frozen, dried, freeze-dried or subject to chemical fixation For instance, tissue samples such as e.g. biopsies may be subjected to formalin fixed and paraffin-embedded (FFPE) chemical fixation. These operations are routinely performed in clinical laboratories, and need not be detailed here. In an embodiment, said biological sample is a FFPE tissue sample. On the other hand, blood-derived samples will most advantageously be stored by freezing.

Once a biological sample is available, it is then possible to isolate the DNA molecules it contains, in particular DNA molecules comprising the at least two specific chromosomal regions expected to be involved in a chromosomal rearrangement.

Isolation of DNA molecules from cell or a tissue sample is only routine procedure well known to those skilled in the art. Standard methods of preparation of a DNA sample include for example DNA extraction by heating or with organic solvents, such as for example phenol, chloroform, isoamyl alcohol or a combination thereof. Commercially available purification reagents and kits can also be used such as kits commercialized by for example, QIAGEN (Valencia, Calif.), Invitrogen (Carlsbad, Calif.), and Stratagene (La Jolla, Calif.). Optionally, the purification can be automated. DNA can be partially or substantially purified from the biological sample.

In some embodiments, such as for example when the biological sample has been submitted to chemical fixation after collection, the method of the invention further comprises a step of preparing the biological sample before isolation of DNA.

By "preparing the biological sample" it is herein referred to treating the biological sample in view of facilitating isolation of DNA. According to the invention, the person skilled in the art can facilitate isolation of DNA by extracting cells or tissues from the biological samples, or by removing chemical from previous fixation treatment.

Preferably, the method of the invention comprises a step of removing paraffin from the FFPE tissue sample. Techniques for removing paraffin before DNA isolation are commonly used by the person skilled in the art. For example, in a typical method for removing paraffin, the tissue is washed several times in xylene to dissolve the paraffin, and then the xylene is removed by performing multiple washes with ethanol before DNA isolation. Those steps are routine work for the person skilled in the art, who can refer for example to Sato et al. for more detailed examples of protocols (*Diagnostic Molecular Pathology;* 10: 4; 265-271; 2001). It is also possible to use commercial solutions (e.g. BiOstic® Paraffin Removal Reagent, MO BIO Laboratories, Carlsbad, Calif. USA). More generally, any method known to the person of skills in the art for removing paraffin is equally convenient.

Once DNA has been isolated, the person skilled in the art can optionally verify that the isolated DNA is appropriate for the intended analysis. For instance, the person skilled in the art can detect whether the isolated DNA actually comprises the said specific chromosomal regions of interest. Thus, in an embodiment, the invention further comprises a step of detecting that the DNA from step a) comprises the specific chromosomal regions. Preferably, detecting that the isolated DNA actually comprises the specific chromosomal regions is performed before or after performing the method of the invention. In another embodiment, detecting that the isolated DNA actually comprises the specific chromosomal regions is performed in a separate analysis.

Any known technique can be used to detect that the DNA molecules isolated from the biological sample comprise the specific chromosomal regions as defined above, such as for example hybridization with oligonucleotide probes capable of hybridizing with the specific chromosomal regions.

By "capable of hybridizing" it is herein referred to the capacity for a polynucleotide of hybridizing with another polynucleotide of a specific sequence at least under standard hybridization conditions, and preferably under stringent conditions. By "hybridization" it is herein referred to the process whereby two polynucleotides undergo base pairing interactions. Two polynucleotides are said to be hybridized when any portion of one polynucleotide is base paired with any portion of the other polynucleotide. It is not necessarily required that the polynucleotides be hybridized across their entire respective lengths. In some embodiments, at least one of the polynucleotide can include portions which are not hybridized to the other polynucleotide. According to the invention, the terms "standard hybridization conditions" refer to conditions under which hybridization of a polynucleotide, such as a probe or a primer, to another polynucleotide, such as a DNA molecule, occurs in the presence of low hybridization temperature and high ionic strength. In one exemplary embodiment, standard hybridization conditions include an aqueous environment containing about 100 mM magnesium sulfate, about 500 mM Tris-sulfate at pH 8.9, and about 200 mM ammonium sulfate at about 50-55° C., or equivalents thereof. The phrase "hybridizing under stringent conditions" refer to conditions under which hybridization of a polynucleotide, such as a probe or a primer, to another polynucleotide, such as a DNA molecule, occurs in the presence of high hybridization temperature and low ionic strength. In one, exemplary embodiment, stringent hybridization conditions include an aqueous environment containing about 30 mM magnesium sulfate, about 300 mM Tris-sulfate at pH 8.9, and about 90 mM ammonium sulfate at about 60-68° C., or equivalents thereof.

In the context of the invention, the DNA molecules isolated in step a) have an average length which is represented by the symbol X.

By "average length of the DNA molecules", it is herein referred to the average length of the DNA molecules which have been isolated from the biological sample. According to the invention, the average length of the DNA molecules is the arithmetic mean of the length of DNA molecules which have been isolated from the biological sample. In the context of the invention, the average length of the DNA molecules is expressed in base pairs. The average length of the DNA molecules in a DNA sample after the isolation step can for example be measured by agarose gel using electrophoresis. Such techniques are quite common to the skilled person and do not need to be further detailed here. For additional information, the skilled person may for instance refer to Sambrook et al.

The average length of the DNA molecule impacts the amplification step. Indeed, the shorter the DNA molecules are, the less likely primers and probes are to hybridize with at least one of those molecules. The inventors have however adapted the design of the primers and of the probes of the invention to the average length of the DNA molecules they target. The average length of the DNA molecules in the biological sample is thus a technical feature of the invention, used to determine other features of the invention, such as the primers used for the amplification step, or some of the probes used in the hybridization step.

According to the invention X is an integer, that is to say a number that can be written without a fractional or decimal component. The average size of DNA molecules after isolation may vary from the isolation technique, and further from the sample they originate from. For example, it is well known that paraffin-embedded tissue sample contains DNA that has been fragmented as a result of the formalin fixation. Paraffin-embedded tissue sample usually contains DNA molecules which average length is inferior or equal to 600 base pairs (Huijsmans1 et al., *BMC Research Notes*, 3:239, 2010), whereas the average length of the cell-free DNA found in blood-derived samples may be inferior or equal to 200 bp (Jahr et al., *Cancer Res.* 61: 1659-1665, 2001; Schwarzenbach et al., *Nat Rev Cancer.* 11(6): 426-437, 2011). Preferably, X is inferior or equal to 600. More preferably, X is inferior or equal to 400. Still more preferably, X is inferior or equal to 350, preferably to 300, more preferably to 250, still more preferably to 200.

The method of the invention is suited for samples comprising DNA molecules of any length, such as FFPE samples that may comprise DNA molecules of an average length of 600 base pairs or less. It is also advantageous to use the method of the invention for detecting chromosomal rearrangements in biological samples containing cell-free DNA, for example in blood-derived samples since they are known to contain DNA fragments with an average length of 200 base pair or less.

Thus, preferably, in the in vitro method for detecting chromosomal rearrangements the DNA molecules are characterized in that they have an average length inferior or equal to 600 base pairs. The method of the invention enables the detection of any rearrangement between two specific regions of interest, even when working with short isolated DNA molecules.

Therefore, the sets of primers of the invention are specifically designed to ascertain that at least one primer will actually hybridize with the DNA comprising the chromosomal rearrangement, even when the DNA molecules isolated from the biological sample are of a particularly short length.

According to the invention, the primers within a set are capable of hybridizing to a nucleic acid strand of one of the said specific chromosomal region. More precisely, all of the primers within a set are capable of hybridizing to the same nucleic acid strand of one of the said specific chromosomal region. In other terms, according to the invention, all of the primers within any specific set of primers hybridize with the same nucleic acid strand of one specific chromosomal region. This first aspect ensures that no spurious amplification takes place within one specific chromosomal region.

The design of the different primers can easily be modified by the person skilled in the art, who can thus adapt the minimal distance between two consecutively hybridized primers according to the expected size of DNA molecules in the sample. The method of the invention thus enables to detect rearrangements even in FFPE samples or blood-derived samples.

By "primers", it is herein referred to any polynucleotide capable of hybridizing with a target sequence of interest and can also serve to prime nucleic acid synthesis. In the context of the invention, the term "primers" refers to single stranded DNA molecules (ssDNA). The primer can become incorporated into the synthesized nucleic acid strand and provide a site to which another primer can hybridize to prime synthesis of a new strand that is complementary to the synthesized nucleic acid molecule. The primer can be composed of any combination of nucleotides or analogs thereof, which may be linked to form a linear polymer of any suitable length. For example, the primer can be a single-stranded oligonucleotide or polynucleotide. Primers sequences vary according to the target sequence of interest. Factors governing the choice of specific primers include, but are not limited to, the G/C content of the primer, the primer length desired, the melting temperature of the primer-target DNA, the selectivity of the primer for the target sequence and the location of the corresponding sequences within the DNA of the target nucleic acid. Those factors are well known from the person skilled in the art.

By "a set of primers", it is herein referred to a plurality of primers comprising at least two primers.

In the context of the invention, each set of primers is capable of hybridizing with a specific chromosomal region, preferably under standard hybridization conditions.

The present invention sets forth sets of primers that can be safely used in particular to detect rearrangements between the ALK gene and the EML4 gene in FFPE samples or blood-derived samples. Those sets of primers can thus also be used to detect the same ALK/ELM4 rearrangement in any type of biological sample, and particularly in biological samples wherein the DNA is scarce and fragmented.

In an embodiment, one of the sets of primers of the invention comprises primers designed to detect rearrangements involving the ALK gene. Preferably, a primer designed to detect rearrangements involving the ALK gene is chosen in the list consisting in primers of sequences SEQ ID No. 6 to 45.

In a preferred embodiment, another set of the sets of primers of the invention comprises primers designed to detect rearrangements involving the EML4 gene. Preferably, a primer designed to detect rearrangements involving the EML4 gene is chosen in the list consisting in primers designed to detect the ALK/ELM4 variant 1 rearrangement, primers designed to detect the ALK/ELM4 variant 2 rearrangement, primers designed to detect the ALK/ELM4 variant 3 rearrangement.

By "ALK/ELM4 variant 1 rearrangement" it is herein referred to the chromosome rearrangement of sequence SEQ ID No.270. Preferably, a primer designed to detect the ALK/ELM4 variant 1 rearrangement is a primer chosen in the list consisting of primers of sequences SEQ ID No. 46 to 102.

By "ALK/ELM4 variant 2 rearrangement" it is herein referred to the chromosome rearrangement of sequence SEQ ID No.271. Preferably, a primer designed to detect the ALK/ELM4 variant 2 rearrangement is a primer chosen in the list consisting of primers of sequences SEQ ID No. 103 to 108.

By "ALK/ELM4 variant 3 rearrangement" it is herein referred to it is herein referred to the chromosome rearrangement of sequence SEQ ID No.272. Preferably, a primer designed to detect the ALK/ELM4 variant 3 rearrangement is a primer chosen in the list consisting of primers of sequences SEQ ID No. 109 to 269.

The present invention also provides sets of primers which can be used for detecting chromosomal rearrangements involving the ROS1. These sets of primers can be safely used in particular to detect rearrangements between the ROS1 gene and any of the CD74, EZR, or SLC34A2 genes in FFPE samples or blood-derived samples. Those sets of primers can thus also be used to detect the same rearrangement between ROS1 and CD74, EZR, or SLC34A2 in any type of biological sample, and particularly in biological samples wherein the DNA is scarce and fragmented.

Thus, in this embodiment, one of the sets of primers of the invention comprises primers designed to detect rearrangements involving the ROS1 gene. Preferably, a primer designed to detect rearrangements involving the ROS1 gene is chosen in the list consisting in primers of sequences SEQ ID No. 365 to 470.

In a preferred embodiment, a set of primers according to the invention comprises primers designed to detect rearrangements involving the ROS1 gene and selected in the list consisting in primers designed to detect the ROS1/CD74 variant 1 rearrangement, primers designed to detect the ROS1/EZR variant 2 rearrangement, primers designed to detect the ROS1/SLC34A2 variant 3 rearrangement.

By "ROS1/CD74 variant 1 rearrangement" it is herein referred to a chromosome rearrangement between the ROS1 gene of sequence SEQ ID NO. 5 and the CD74 gene of sequence SEQ ID No. 312. Preferably, a primer designed to detect the ROS1/CD74 variant 1 rearrangement is a primer chosen in the list consisting of primers of sequences SEQ ID No. 315 to 328 and SEQ ID No. 433 to 451.

By "ROS1/EZR variant 2 rearrangement" it is herein referred to the chromosome rearrangement between the ROS1 gene of sequence SEQ ID NO. 5 and the EZR gene of sequence SEQ ID No. 313. Preferably, a primer designed to detect the ROS1/EZR variant 2 rearrangement is a primer chosen in the list consisting of primers of sequences SEQ ID No. 329 to 336 and SEQ ID No. 433 to 451.

By "ROS1/SLC34A2 variant 3 rearrangement" it is herein referred to it is herein referred to the chromosome rearrangement between the ROS1 gene of sequence SEQ ID NO. 5 and the SLC34A2 gene of sequence SEQ ID No. 314. Preferably, a primer designed to detect the ROS1/SLC34A2 variant 3 rearrangement is a primer chosen in the list consisting of primers of sequences SEQ ID No. 337 to 432.

The sets of primers are used in a multiplex polymerase chain reaction assay to amplify the DNA molecules in the sample, in particular the DNA molecules that comprise the rearrangement of interest.

By "amplifying" it is herein referred to any action or process whereby at least a portion of a first polynucleotide (also referred to as a template polynucleotide) is replicated or copied into at least one additional polynucleotide. The additional polynucleotide optionally has a sequence that is substantially identical or substantially complementary to at least some portion of the polynucleotide. By "substantially identical", it is herein referred to two polynucleotides which sequences have at least 99% identity. According to the invention, two polynucleotides are "substantially complementary", when the sequence of one polynucleotide has at least 99% identity with the complementary sequence of the other polynucleotide.

The template polynucleotide of the amplification reaction can be single-stranded or double-stranded and the resulting additional polynucleotides can independently be single-stranded or double-stranded. In some embodiments, amplification includes an enzyme-catalyzed reaction for the production of at least one copy of at least some portion of the template polynucleotide or the production of at least one copy of a polynucleotide that is complementary to at least some portion of the template polynucleotide.

According to the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/bl2.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

By "amplifying the DNA molecules", it is herein referred to generating one or more copies of said DNA molecule, using the DNA molecule as a template.

In the context of the invention, amplifying the DNA molecules is achieved by multiplex polymerase chain reaction assay.

By "multiplex polymerase chain reaction assay", it is herein referred to any assay based on the polymerase chain reaction assay and wherein amplifications of more than two DNA molecules, and comprising more than two distinct primer sets, are simultaneously achieved in the same reaction volume. Such techniques have been long known from the skilled person, who may refer to Chamberlain et al. for further details (*Nucleic Acids Research;* 16 (23): 11141-11156, 1988).

Generally, amplification by polymerase chain reaction requires specific conditions that include a catalyst for amplification or for nucleic acid synthesis, for example a polymerase, a primer at least partially complementary to the nucleic acid to be amplified, and nucleotides, such as deoxyribonucleotide triphosphates (dNTPs) to promote extension of the primer once hybridized to the nucleic acid.

The amplification conditions may require hybridization or annealing of a primer to a nucleic acid, extension of the primer, and a denaturing step in which the extended primer is separated from the nucleic acid sequence undergoing amplification. Typically, but not necessarily, amplification conditions include a plurality of cycles where the steps of annealing, extending and separating are repeated. Typically, the amplification conditions include cations such as Mg++ or Mn++.

It is well known to the person skilled in the art that DNA amplification may yield undesired amplification products due to spurious priming. The method of the invention overcomes this technical issue by adding a step, further to the amplification step, wherein the amplification product is hybridized with at least one set of nucleic acid probes.

This step enables to select the amplification product of interest and to discard amplification spurious amplification products due to. This step thus ensures that said amplification product actually corresponds to the expected product of the amplification of step b). By "expected product of the amplification of step b)", it is herein referred to the polynucleotide which sequence would result from the amplification of a chromosomal rearrangements between the at least two reference chromosomal regions.

By "the product of the amplification of step b)" it is herein referred to polynucleotides that contain: a) a first segment that is complementary to the first strand of the first specific chromosomal region to which a first primer binds, and b) a second segment that is complementary to the second strand of the second specific chromosomal region to which a second primer binds. The junction between the two segments corresponds to the rupture point of a chromosomal rearrangement.

By "probe", it is herein referred to a nucleic acid that is complementary to a nucleotide sequence of interest. In the context of the invention, a probe is a nucleic acid that is complementary to the product of the amplification of step b).

According to the invention, any nucleic probes capable of hybridizing with the product of the amplification of step b), that is to say any nucleic probes complementary to the expected product of the amplification of step b) can be used.

However, the skilled person can specifically design the nucleic acid probes in order to decrease the probability that said nucleic acid probes will hybridize with undesirable amplification artifacts.

For instance, since the amplification of step b) uses primers capable of hybridizing to a nucleic acid strand of one of the said specific chromosomal regions, the expected product of amplification is also capable of hybridizing to the same nucleic acid strand. By selecting nucleic probes capable of hybridizing to the first nucleic acid strand of one of the said reference chromosomal regions, the person skilled in the art ensures that the probes of the invention will not hybridize with undesirable amplification artifacts from non-targeted chromosomal region.

Moreover, since the exact location of the rupture point of a chromosomal rearrangement cannot be predicted, the amplification products will be expected to comprise a new rearrangement of the two specific regions of interest, yet the new junction between those two regions will be difficult to anticipate. If their design does not take this aspect into account, some probes may simply not hybridize with the amplification product, thus decreasing the sensitivity of the method of the invention.

The inventors have found that it is possible to increase the sensitivity of the method by selecting, for the hybridization step, nucleic acid probes that are capable of hybridizing at a close base pair distance from at least one of the primers being used for the amplification step. This technical feature contributes to decrease the probability that the nucleic acid probes of the invention hybridize with spurious amplification products. The base pair distance between nucleic acid probes according to the invention corresponds to the distance the 5' end of a probe and the 3' end of the closest primer capable of hybridizing to the same specific chromosomal region. Preferably, the base pair distance between nucleic acid probes is of between 0 to 30 bases.

In a preferred embodiment of the invention, said set of nucleic acid probes comprises a plurality of nucleic acid probes,
   said probes being capable of hybridizing to a nucleic acid strand of one of the said specific chromosomal regions at sites regularly spaced of less than X/2 base pairs; and
   the 5'end of said probe being capable of hybridizing within 0 to 30 bases from the 3'end of a primer capable of hybridizing to the same specific chromosomal region.

In a preferred embodiment, said probes are designed to hybridize to a specific chromosomal region comprising at least the anaplastic lymphoma kinase gene (ALK) of sequence SEQ ID No.1. In another preferred embodiment, said probes are designed to hybridize to a specific chromosomal region comprising at least the proto-oncogene tyrosine-protein kinase gene ROS1 of sequence SEQ ID No.5.

Preferably, a probe designed to hybridize to a specific chromosomal region comprising at least the anaplastic lymphoma kinase gene (ALK) of sequence SEQ ID No.1 is a probe chosen in the list consisting of probes of sequences SEQ ID No. 273 to 311, whereas a probe designed to hybridize to a specific chromosomal region comprising at least the proto-oncogene tyrosine-protein kinase gene ROS1 of sequence SEQ ID No.5 is a probe chosen in the list consisting of probes of sequences SEQ ID No. 452 to 470.

In an embodiment, the method further comprises a step of detecting the hybridization of step c).

According to the invention, the hybridization step can be performed according to various techniques. The skilled person may use for example surface-based hybridization, wherein the probes are immobilized on a substrate, or solution hybridization, wherein the probes and their targets are both in solution. Immobilized probes are convenient whenever multiplexing is contemplated, as they can facilitate detection of the hybridization. In a first embodiment, the probe is thus immobilized on a substrate prior to hybridization, or on a surface of a substrate. In a specific embodiment, the probe is immobilized on a surface of a planar support. In another embodiment, the probe is in solution. Thus, in a preferred embodiment, the hybridization step is performed in solution. Indeed, it has been shown however that hybridization on a solid surface is less efficient than solution hybridization (Peterson et al. 2002; Peplies et al. 2003).

In order to take full advantage of the hybridization step, the skilled person can further detect this hybridization.

In an embodiment, the method of the invention further comprises a step of detecting the hybridization of step c).

Detecting the hybridization of step c) can be achieved by any technique known of the skilled person. For example, to detect hybridization of the probe to the product of the amplification of step b), the person skilled in the art can tag (or "label") the probe with a molecular marker of either radioactive or fluorescent molecules. Commonly used molecular markers are the radioactive isotope of phosphorus $^{32}P$, which can be incorporated into the phosphodiester bond in the probe DNA, or digoxigenin, which is a non-radioactive, antibody-based marker. Oligonucleotides, such as the product of the amplification of step b), that have moderate to high sequence similarity to the probe are then detected by visualizing the hybridized probe via autoradiography or other imaging techniques. In an embodiment, the probe is tagged with a molecular marker.

In order to increase the sensitivity of the method, the skilled person may decide to use other techniques of detection, such as sequencing or mass spectrometry.

Mass spectrometry is particularly interesting since it distinguishes between polynucleotides that differ in as little as one nucleotide residue. Mass spectrometry can be used to distinguish between two polynucleotides that have the same size, if they have a different composition in nucleotide residues. Mass spectrometry can also differentiate between polynucleotides of different sizes. Thus, preferably, the detection is performed by mass spectrometry.

The method of the invention thus leads to the rapid and easy detection of any chromosomal rearrangement. In addition, it is possible to determine the breakage point for each rearrangement by sequencing. In other words, it is possible for each patient to precisely identify the point where the break occurred. This information is particularly advantageous, since it could help design a specific treatment for each patient. However, the method of the prior art cannot provide clinicians with this information. In particular, RNA-based techniques are useless in this respect.

Thus in a preferred embodiment, the method of the invention comprises a further step of sequencing the polynucleotide molecules resulting from the amplification of step b). It will immediately be clear to the person of skills in the art that the sequencing step is more advantageously performed on the amplicons hybridizing with the probes described hereabove. Thus, in a more preferred embodiment, said further step of sequencing takes place after step c) of the method of the invention. In this specific embodiment, it will be particularly useful to perform the sequencing step with the primer which is closest to the hybridizing probe. As understood herein, the "closest" primer refers to the primer whose 3' end is separated by the fewest number of nucleotides from the 5' end of said probe.

The skilled person may thus use mass spectrometry directly on the amplification products hybridized with the probes. The use of mass spectrometry for the analysis of nucleic acids has been long known from the person skilled in the art, and has been reviewed for example in Crain et al. (*Mass Spectrometry Reviews*, 9, 505-554; 1990). Mass spectrometry method and apparatus appropriate for detecting polynucleotides have been developed by the company Sequenom, some of which have been thoroughly described in patent applications U.S. Pat. No. 7,501,251, WO 1997037041, or U.S. Pat. No. 7,198,893.

In order to increase the confidence of the method of detection, the skilled person can use mass spectrometry after an additional step of elongation of the probes. When the person skilled in the art performs an elongation step after the hybridization step, only probes that are capable of actually hybridizing to an amplification product will be elongated. Probes that have been elongated can easily be differentiated from probes that have not been elongated by mass spectrometry, and this information can further indicate if the amplification product corresponds to the expected amplification product. Hence, the step of elongation of the probes further increases the sensitivity of the method. Preferably, the method further comprises a step of nucleotide elongation prior to detection performed by mass spectrometry.

Many chromosomal rearrangements are correlated with cancers. More particularly, chromosomal rearrangements involving the ALK gene or the ROS1 gene are particularly correlated with NSCLC. Moreover, most cancer diagnosis are performed on biological samples wherein the DNA is fragmented, such as FFPE samples or blood-derived samples. The method for of the invention is particularly advantageous detecting rearrangements in such samples, and can therefore usefully be used for diagnosing cancers.

Another object of the invention is the use of the method for detecting chromosomal rearrangements of the invention for the in vitro diagnostic or subclassification of cancer, for example of NSCLC, in a human subject.

Another object of the invention is an in vitro method for diagnosing cancer, preferably of NSCLC, more preferably that comprise a chromosomal rearrangement involving the gene ALK or the gene ROS1, in a human subject, said method comprising detecting chromosomal rearrangements between at least two reference chromosomal regions in a biological sample of said human subject according to the method of the invention, wherein said specific chromosomal regions comprise at least the anaplastic lymphoma kinase gene (ALK) of sequence SEQ ID No.1 or the proto-oncogene tyrosine-protein kinase gene ROS1 of sequence SEQ ID No.5.

In an embodiment, the in vitro method for diagnosing or subclassification of cancer comprises detecting chromosomal rearrangements between at least two reference chromosomal regions in a biological sample of said human subject with the method of the invention, wherein said specific chromosomal regions comprise at least the anaplastic lymphoma kinase gene (ALK) of sequence SEQ ID No.1 and the echinoderm microtubule-associated protein-like 4 gene (EML4) of sequence SEQ ID No.4.

In another embodiment, the in vitro method for diagnosing cancer comprises detecting chromosomal rearrangements between at least two reference chromosomal regions in a biological sample of said human subject with the method of the invention, wherein said specific chromosomal regions comprise at least the proto-oncogene tyrosine-protein kinase gene ROS1 of sequence SEQ ID No.5 and any one of the CD74 gene (CD74) of sequence SEQ ID No.312, the EZR gene (EZR) of sequence SEQ ID No.313, and the SLC34A2 gene (SLC34A2) of sequence SEQ ID No.314.

The method for diagnosing or subclassification of cancer can further comprise a step wherein cancer is diagnosed in said human subject if a chromosomal rearrangement is detected in said biological sample.

Therefore, in an embodiment, the in vitro method for diagnosing or subclassification of cancer in a human subject comprises:
  a) detecting chromosomal rearrangements between at least two reference chromosomal regions in a biological sample of said human subject according to the method of the invention;
  b) diagnosing cancer in said human subject if a chromosomal rearrangement has been detected in step a).

The invention enables detecting chromosomal rearrangements, in particular chromosomal rearrangements involving the anaplastic lymphoma kinase gene (ALK) or the proto-oncogene tyrosine-protein kinase gene ROS1 of sequence SEQ ID No.5. As such, this method is particularly suited for selecting subjects for clinical tests.

Additionally, the method for detecting chromosomal rearrangements of the invention can be used to select the subjects that are the more likely to benefit from a specific treatment, in particular anti-cancer therapy. As such, it can advantageously be used in determining the prognosis or prediction of a response to a treatment, or be incorporated into methods of treatments.

Therefore, another object of the invention is a method for selecting subjects likely to benefit from a specific treatment:
  a) detecting chromosomal rearrangements between at least two reference chromosomal regions in a biological sample of said human subject according to the method of the invention;
  b) diagnosing cancer in said human subject if a chromosomal rearrangement has been detected in step a);
  c) selecting the subject as likely to benefit from a specific treatment, in particular anti-cancer therapy if a cancer has been diagnosed in step b).

Still another object of the invention is a method for the treatment of cancer in a human subject in need thereof, comprising diagnosing cancer in a human subject with the method of the invention and administering an effective amount of anti-cancer therapy to said subject.

Therefore, in an embodiment, the method for the treatment of cancer in a human subject comprises:
  a) detecting chromosomal rearrangements between at least two reference chromosomal regions in a biological sample of said human subject according to the method of the invention;
  b) diagnosing cancer in said human subject if a chromosomal rearrangement has been detected in step a);
  c) administering an effective amount of anti-cancer therapy to said subject if a cancer has been diagnosed in step b).

According to the invention, the terms "anti-cancer therapy" refers to any type of drug aiming at treating cancer in a human subject. Anti-cancer therapy includes chemotherapeutic drugs and targeted therapy.

According to the invention, chemotherapeutic drugs comprise inter alia alkylating agents, antimetabolites, anthracyclines, plant alkaloids, and topoisomerase inhibitors.

According to the invention, alkylating agents are agents capable of alkylating nucleophilic functional groups under normal conditions present in cells. Alkylating agents comprise cisplatin, carboplatin, oxaliplatin, mechlorethamine, cyclophosphamide, chlorambucil, and ifosfamide.

According to the invention, antimetabolites are agents capable of inhibiting the activity of a metabolite. Such substances are often similar in structure to the metabolite that they interfere with. Antimetabolites comprise 5-flurouracil (5-FU), 2-fluoro-ara-amp (fludarabine), and methotrexate.

According to the invention, anthracyclines are molecules derived from *Streptomyces* bacterium *Streptomyces peucetius* var. *caesius*. Anthracyclines comprise daunorubicin, doxorubicin, epirubicin, idarubicin, valrubicin, and mitoxantrone.

According to the invention, plant alkaloids are alkaloids, that is to say chemical compounds comprising basic nitrogen atoms, which are derived from plants. Plant alkaloids comprise vinblastine, vincristine, vindesine, vinorelbine, paclitaxel (taxol) and docetaxel (taxotere).

According to the invention, topoisomerase inhibitors are molecules capable of inhibiting type I or type II human topoisomerases. Topoisomerase inhibitors comprise topoisomerase type I inhibitors such as for example irinotecan and topotecan and type II inhibitors such as for instance amsacrine, etoposide, etoposide phosphate, and teniposide.

According to the invention, a targeted therapy is a type of therapy that blocks the growth of cancer cells by interfering with specific targeted molecules needed for carcinogenesis and tumor growth, rather than by interfering with all rapidly dividing cells. Targeted therapy comprises small molecules and monoclonal antibodies.

According to the invention, small molecules comprises tyrosine-kinase inhibitors such as imatinib, gefitinib, erlotinib, bortezomib (velcade), tofacitinib, crizotinib, AP26113, LDK378, obatoclax, ABT-263, gossypol, iniparib, olaparib, PI3K inhibitors, apatinib, AN-152, vemurafenib, dabrafenib, LGX818, trametinib, MEK162, PD-0332991, and LEE011.

According to the invention, monoclonal antibodies comprise rituximab, trastuzumab, cetuximab, and bevacizumab.

The invention is particularly adapted for detecting non-small cell lung cancers that comprise a chromosomal rearrangement involving the gene ALK. Those cancers do not respond well to chemotherapeutic drugs or radiation therapy but respond very well to ALK inhibitors. Likewise, the invention enables detecting non-small cell lung cancers that comprise a chromosomal rearrangement involving the gene ROS1, since these cancers are expected to be particularly sensitive to ROS1 inhibitors. It is therefore crucial to be able to provide the appropriate therapy in particular to those subjects that harbor chromosomal rearrangement involving the gene ALK or the gene ROS1.

In an embodiment, the method is for the treatment of non-small cell lung cancers, preferably that comprise a chromosomal rearrangement involving the gene ALK or the gene ROS1, wherein the method comprises diagnosing non-small cell lung cancers that comprise a chromosomal rearrangement involving the gene ALK or the gene ROS1 in a human subject with the method of the invention and administering a therapeutically effective amount of ALK inhibitors and/or ROS1 inhibitors to said subject.

According to the invention, ALK inhibitors are agents capable of inhibiting the anaplastic lymphoma kinase (ALK). ALK inhibitors comprise crizotinib, AP26113, and LDK378. Preferably, the ALK inhibitor of the invention is crizotinib, since crizotinib is also known to be an inhibitor of ROS1.

According to the invention, the terms "a therapeutically effective amount" refer to the minimum concentration or amount of a compound (or of compounds) which is effective to prevent, alleviate, reduce or ameliorate symptoms of disease or prolong the survival of the patient being treated. A therapeutically effective amount is also one in which any toxic or detrimental effects of the agent are outweighed by the therapeutically beneficial effects. More particularly, in reference to the treatment of cancer, a therapeutically effective amount refers to that amount which has the effect of (1)

reducing the size of (or preferably eliminating) the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with the cancer.

It is understood that the effective amount will be adapted by the skilled person according to the usual criteria such as for example the age, sex, health, and body weight of the subject.

Other objects of the invention are kits comprising for implementing the methods of the invention, comprising means appropriate for detecting chromosomal rearrangements between at least two specific chromosomal regions in a biological sample of a human subject. More preferably, the kits of the invention comprise means appropriate for detecting chromosomal rearrangements between at least two specific chromosomal regions in a biological sample of a human subject, wherein said specific chromosomal regions comprise at least the anaplastic lymphoma kinase gene (ALK) of sequence SEQ ID No.1 or the proto-oncogene tyrosine-protein kinase gene ROS1 of sequence SEQ ID No.5. Even more preferably, the kits of the invention comprise means appropriate for detecting chromosomal rearrangements between at least two specific chromosomal regions in a biological sample of a human subject, wherein said specific chromosomal regions comprise at least the anaplastic lymphoma kinase gene (ALK) of sequence SEQ ID No.1 and the echinoderm microtubule-associated protein-like 4 gene (EML4) of SEQ ID No.4; alternatively, the kits of the invention comprise means appropriate for detecting chromosomal rearrangements between at least two specific chromosomal regions in a biological sample of a human subject, wherein said specific chromosomal regions comprise at least the proto-oncogene tyrosine-protein kinase gene ROS1 of sequence SEQ ID No.5 and any one of the CD74 gene (CD74) of sequence SEQ ID No.312, the EZR gene (EZR) of sequence SEQ ID No.313, and the SLC34A2 gene (SLC34A2) of sequence SEQ ID No.314.

Means appropriate for detecting chromosomal rearrangements comprise for example primers and probes appropriate for detecting chromosomal rearrangements according to the invention. In an embodiment, the kits of the invention comprise primers or probes capable of hybridizing with the anaplastic lymphoma kinase gene (ALK) of sequence SEQ ID No.1. Preferably, the kits of the invention comprise primers and probes capable of hybridizing with the anaplastic lymphoma kinase gene (ALK) of sequence SEQ ID No.1. Preferably, the kits of the invention further comprise primers or probes capable of hybridizing with the echinoderm microtubule-associated protein-like 4 gene (EML4) of SEQ ID No.4. More preferably, the kits of the invention further comprise primers and probes capable of hybridizing with the echinoderm microtubule-associated protein-like 4 gene (EML4) of SEQ ID No.4.

In another embodiment, the kits of the invention comprise primers or probes capable of hybridizing with the proto-oncogene tyrosine-protein kinase gene ROS1 of sequence SEQ ID No.5. Preferably, the kits of the invention comprise primers and probes capable of hybridizing with the proto-oncogene tyrosine-protein kinase gene ROS1 of sequence SEQ ID No.5. Preferably, the kits of the invention further comprise primers or probes capable of hybridizing with at least one of the CD74 gene (CD74) of sequence SEQ ID No.312, the EZR gene (EZR) of sequence SEQ ID No.313, and the SLC34A2 gene (SLC34A2) of sequence SEQ ID No.314. More preferably, the kits of the invention further comprise primers and probes capable of hybridizing with at least one of the CD74 gene (CD74) of sequence SEQ ID No.312, the EZR gene (EZR) of sequence SEQ ID No.313, and the SLC34A2 gene (SLC34A2) of sequence SEQ ID No.314.

The following examples are given by way of illustration only and are not, unless otherwise stated, intended to be limiting.

EXAMPLE

Example 1

The ALK/EML4 chromosomal rearrangement was detected as described herebelow.

1. A first round of PCR was performed, in order to amplify the DNA comprising the chromosome rearrangement.

A first premix PCR was prepared using the reagents from the kit 10x96 iPlex Pro Set Genotyping reagents (Sequenom).

For each PCR condition, 2 µl of the PCR mix were prepared in the following proportions:

| Product | Volume |
| --- | --- |
| H2O | 0.8 µl |
| 10X PCR Buffer | 0.5 µl |
| MgCl2 25 mM | 0.4 µl |
| dNTPs 25 mM | 0.1 µl |
| Sequenom PCR enzyme 5 U/µl | 0.2 µl |

The 2 µl of premix was added into four tubes. In each tube, 1 µl of a specific mix of primers (either mix A, mix B, mix C or mix D) was added.

Each mix of primers comprises a set of 38 primers hybridizing with ALK ("forward primers") and a maximum of 40 primers hybridizing with EML4 ("reverse primers").

2 µl of DNA (at a concentration of about 10 ng/µl) from the biological sample of a subject was then added to each tube.

The PCR was performed under the following conditions
1. 94° C. for 2 min;
2. Then 45 cycles of:
　94° C. for 30 sec
　56° C. for 30 sec
　72° C. for 1 min
3. Then, 72° C. for 5 min,
4. Finally, 4° C. until further analysis 2. The product of the PCR is then treated with SAP (Shrimp Alkaline Phosphatase)

2 µl of SAP mix was prepared for each PCR described above, according to the following proportions:

| Product | Volume |
| --- | --- |
| H2O | 1.53 µl |
| SAP 10X Buffer | 0.17 µl |
| SAP enzyme | 1.7 U/µl |

The 2 µl of mix were added to each PCR volume.

The following cycle was completed: 37° C. for 40 min, 85° C. for 5 min, and finally 4° C. until further analysis.

3. The amplification products of each PCR were hybridized with probes which sequence is adjacent to the 38 primers hybridizing with ALK. A second PCR was performed, to obtain an extension of the probes that have actually hybridized with the amplification products.

The mix of probes comprises the probes of sequence SEQ ID No. 273 to 311.

2 µl of a second premix PCR mix was prepared for each PCR described above, in the following proportions:

| Product | Volume |
|---|---|
| H2O | 0.755 µl |
| iPlex Pro Buffer 10X | 0.2 µl |
| iPlex Pro Term Mix 10X | 0.2 µl |
| iPlex Pro enzyme 33 U/µl | 0.041 µl |
| Probe Mix | 0.804 µl |

The 2 µl of mix were added to each of the previously described PCR volume.

The PCR was performed under the following conditions 5. 94° C. for 30 sec;
6. Then 40 cycles of:
   94° C. for 5 sec, followed by 5 sub-cycles of
      52° C. for 5 sec
      80° C. for 5 sec
7. Then, 72° C. for 3 min,
8. Finally, 4° C. until further analysis The content of each PCR tube is then transferred on chips for mass spectrometry reading on Sequenom's MassARRAY® Analyzer 4. This transfer is carried out using the Sequenom's MassARRAY® Nanodispenser.

Example 2

The same experiment as in example 1 was performed for detecting ROS1/CD74, ROS1/EZR and ROS1/SLC34A2 variants. The primers used were the primers of sequence of sequences SEQ ID No. 315 to 328 and SEQ ID No. 433 to 451 for the ROS1/CD74 variant, SEQ ID No. 329 to 336 and SEQ ID No. 433 to 451 for the ROS1/EZR variant, and SEQ ID No. 337 to 432 for the ROS1/SLC34A2 variant. The amplification conditions were the same as in example 1.

A ROS1/SLC34A2 rearrangement was successfully detected using probes specific for this variant (SE QID No. 471-487) whereas the two other variants gave no signal with the same probes. In addition, about 30 DNA which were classified as negative (no translocation including ROS1) by FISH were confirmed to be negative with each of the 3 variants.

Example 3

Sequencing was performed on the ROS1/SLC34A2 DNA of example 2, either after the first step of amplification, or after the detection step. The primer used was SLC34A2-7 (SEQ ID NO. 343), the closest to the probe SLC34A2-7 SEQ ID No. 477) which gave the strongest hybridization signal in the experiment of example 2.

For sequencing purposes, 10 µL of the amplification reaction were first purified "QIAquick PCR purification kit" (Qiagen). The sequencing reaction was then performed using the BigDye Terminator Kit (1.1 or 3.1) of Applied Biosystems, and the products were analyzed with the ABI3130xl sequencer of Applied Biosystems. The same sequence of the breakage point was obtained and is displayed in SEQ ID No. 494.

The inventors were equally capable of obtaining the sequence of the breaking point when using a primer (SLC34A2-6: SEQ ID NO. 342) farther from the positive probe, although the intensity of the sequencing signal was lower as expected.

Example 4

In order to assess the effect of the positioning of the probe in respect to the amplification primers, the following experiment was performed.

When the DNA is of good quality, a smaller distance between the probe and the primer is expected to lead to higher sensitivity. This is even more important when the DNA is fragmented, since the size of the potential amplicons is already small. Thus, in this case, only a probe close enough to the primer will be capable of hybridizing with the amplification product.

This was experimentally demonstrated on DNA isolated from a cell line positive for the translocation ROS1/SLC34A2. A negative control with respect to the translocation was used. The primers/probes used were either close (group 1) or remote (group 2). The same primers were used, but the probes of group 2 (SEQ ID No. 488 to 493) were shifted by at least 60-bp with respect to the probes of group 1 (SEQ ID No. 472 to 478).

Results are shown in Table 1.

TABLE 1 the results are compared between a positive sample and a negative control with a set of probes close to the amplification primers (group 1) and a set of probes further away from said primers (group 2). The results are expressed as units of signal intensity (positive above 0.15).

| | Group 1 probes | | Group 2 probes | |
|---|---|---|---|---|
| | Positive sample | Negative control | Positive sample | Negative control |
| Probe 2 | 0.08 | 0.02 | 0.09 | 0.09 |
| Probe 3 | 0.47 | 0.01 | 0.27 | 0.01 |
| Probe 5 | 1.92 | 0.03 | 1.38 | 0.00 |
| Probe 6 | 3.12 | 0.11 | 3.24 | 0.00 |
| Probe 7 | 5.25 | 0.00 | 0.09 | 0.01 |
| Probe 8 | 0.00 | 0.01 | 0.02 | 0.06 |

With the probes of group 1, a positive result is observed with 4 consecutive probes (4, 5, 6 and 7), whereas the more distant probes of group 2, only 3 consecutive probes are positive (4, 5 and 6). Probe 7 which yields the stronger signal with the probes of group 1 is thus no longer detectable when the probes are too far away from the primers. Decreasing the distance between the primers and the probes is thus crucial for improving significantly the sensitivity of the method.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10385401B2). An electronic copy of the "Sequence Listing" will also be available from the USPTO upon request and payment of the fee set forth in 37 CFR 1.19(b)(3).

The invention claimed is:

1. An in vitro method for detecting chromosomal rearrangements between at least two specific chromosomal regions in a biological sample of a human subject, wherein said rearrangement is a ELM4-ALK, ROS1-CD74, ROS1-EZR, or ROS1-SLC34A2 chromosomal rearrangement, said method comprising the steps of:
   a) isolating deoxyribonucleic acid (DNA) molecules comprising said specific chromosomal regions from said biological sample, wherein said DNA molecules have an average length of X base pairs;
   b) amplifying the DNA molecules of step a) by a multiplex polymerase chain reaction assay,
   said assay comprising at least two sets of primers, wherein each set of primers is capable of hybridizing with a specific chromosomal region, and
   each set of primer comprises a plurality of primers,
   said primers being capable of hybridizing to a nucleic acid strand of one of the said specific chromosomal regions at sites regularly spaced of less than X/2 base pairs; and
   c) hybridizing the product of the amplification of step b) with at least one set of nucleic probes,
wherein said set of nucleic acid probes comprises a plurality of nucleic acid probes,
   said probes being capable of hybridizing to a nucleic acid strand of one of the said specific chromosomal regions at sites regularly spaced of less than X/2 base pairs; and
   the 5' end of said probe being capable of hybridizing within 0 to 30 bases from the 3' end of a primer capable of hybridizing to the same specific chromosomal region; and
wherein the successful hybridization of at least one probe of said set of nucleic probes to product of the amplification of step b) indicates the presence of a chromosomal rearrangement.

2. The method of claim 1, wherein X is inferior or equal to 600.

3. The method of claim 1, wherein said biological sample is a formalin-fixed, paraffin-embedded (FFPE) tissue sample or a blood-derived sample.

4. The method of claim 1, wherein said biological sample is a tumor tissue.

5. The method of claim 4, wherein said tumor is selected from the group consisting of carcinoma, including that of the bladder, breast, colon, kidney, liver, lung, ovary, pancreas, stomach, cervix, thyroid and skin; including squamous cell carcinoma; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma.

6. The method of claim 5, wherein the said tumor is a lung tumor.

7. The method of claim 1, further comprising a step of detecting the hybridization of step c).

8. The method of claim 7, wherein said detection is performed by mass spectrometry.

9. The method of claim 1, said method further comprising a step of sequencing the product of amplification of step b).

10. The method of claim 1, said method being for detecting chromosomal rearrangements between two specific chromosomal regions.

11. The method of claim 1, wherein said specific chromosomal regions comprise at least the anaplastic lymphoma kinase gene (ALK) of sequence SEQ ID No.1.

12. The method of claim 11, wherein said specific chromosomal regions further comprise the echinoderm microtubule-associated protein-like 4 gene (EML4) of SEQ ID No.4.

13. The method of claim 1, wherein said specific chromosomal regions further comprise the ROS1 gene of sequence SEQ ID No.5.

14. An in vitro method for diagnosing cancer, wherein the method comprises detecting chromosomal rearrangements between at least two specific chromosomal regions in a biological sample of said human subject with the method of claim 1.

15. The method of claim 14, wherein said cancer is non-small cell lung cancer.

16. The method of claim 14, wherein said specific chromosomal regions comprise at least the ROS1 gene of sequence SEQ ID No.5 and at least one of the CD74 gene (CD74) of sequence SEQ ID No.312, the EZR gene (EZR) of sequence SEQ ID No.313, and the SLC34A2 gene (SLC34A2) of sequence SEQ ID No.314.

17. The method of claim 14, wherein said method comprises:
   a) detecting chromosomal rearrangements between at least two specific chromosomal regions in a biological sample of said human subject;
   b) diagnosing cancer in said human subject if a chromosomal rearrangement has been detected in step a).

18. A method for the treatment of cancer in a human subject in need thereof, comprising diagnosing cancer in a human subject with the method of claim 14 and administering an effective amount of anti-cancer therapy to said subject.

19. The method of claim 18 comprising diagnosing non-small cell lung cancers that comprise a chromosomal rearrangement involving the gene ALK or the gene ROS1 in a human subject and administering an effective amount of ALK inhibitors to said subject.

* * * * *